(12) United States Patent
Aloise et al.

(10) Patent No.: US 7,448,867 B2
(45) Date of Patent: Nov. 11, 2008

(54) MEDICAL TREATMENT APPARATUS

(75) Inventors: Carlos A. Aloise, Alta Loma, CA (US); William X. Du, Walnut, CA (US); L. Stephen Buchanan, Santa Barbara, CA (US); Steven E. Benson, La Verne, CA (US); Brenton C. Lively, Orange, CA (US); Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 11/229,463

(22) Filed: Sep. 16, 2005

(65) Prior Publication Data

US 2006/0063126 A1 Mar. 23, 2006

Related U.S. Application Data

(60) Provisional application No. 60/611,187, filed on Sep. 17, 2004.

(51) Int. Cl.
*A61C 5/02* (2006.01)

(52) U.S. Cl. .............................. 433/81; 433/32; 433/90; 222/146.5

(58) Field of Classification Search .................. 433/81, 433/89, 90, 114, 116, 32; 222/146.5
See application file for complete search history.

(56) References Cited

U.S. PATENT DOCUMENTS

| | | | |
|---|---|---|---|
| 3,295,514 A * | 1/1967 | Hein et al. ..................... | 433/81 |
| 3,831,815 A | 8/1974 | Glasgow | |
| 3,951,308 A | 4/1976 | Thirtle | |
| 4,065,034 A | 12/1977 | Callan | |
| 4,265,618 A | 5/1981 | Herskovitz et al. | |
| 4,330,280 A | 5/1982 | Dougherty et al. | |
| 4,357,136 A | 11/1982 | Herskovitz et al. | |

(Continued)

FOREIGN PATENT DOCUMENTS

DE  29515040 U1  3/1997

(Continued)

OTHER PUBLICATIONS

European Patent Office, International Search Report and Written Opinion, May 9, 2006.

(Continued)

*Primary Examiner*—Ralph A Lewis
(74) *Attorney, Agent, or Firm*—Wood, Herron & Evans, L.L.P.

(57) ABSTRACT

An apparatus for dispensing material during a dental or endodontic procedure includes a housing having a motor with an output. A needle heating member including a chamber may receive a prefilled needle of dispensing material. A heater at least substantially surrounds the chamber for heating the material in the needle. A plunger is used to expel the material from the needle during activation of the motor. A reusable protective sheath is provided for disposition on the outside of the housing. A method of manufacturing a needle for use and dispensing a material during a dental or endodontic procedure includes drawing a blank of metal having a closed distal end, bending the blank at a desired angle, and removing a portion of the drawn metal from the distal end to open the distal end thereby forming the dispensing needle.

9 Claims, 10 Drawing Sheets

U.S. PATENT DOCUMENTS

| | | | |
|---|---|---|---|
| 4,384,852 A | 5/1983 | Yamauchi et al. | |
| 4,455,858 A | 6/1984 | Hettich | |
| 4,472,141 A | 9/1984 | Dragan | |
| 4,582,488 A | 4/1986 | Newman | |
| 4,684,334 A | 8/1987 | Gargas | |
| 4,684,344 A * | 8/1987 | Brockway et al. | 433/81 |
| 4,704,088 A | 11/1987 | Newman | |
| 4,790,254 A | 12/1988 | Vorholt | |
| 4,974,752 A | 12/1990 | Sirek | |
| 5,026,187 A | 6/1991 | Belanger et al. | |
| 5,061,179 A | 10/1991 | Drgan | |
| 5,125,836 A | 6/1992 | Dragan et al. | |
| 5,197,875 A | 3/1993 | Nerli | |
| 5,236,269 A | 8/1993 | Handy | |
| 5,269,762 A | 12/1993 | Armbruster et al. | |
| 5,306,147 A | 4/1994 | Dragan et al. | |
| 5,336,088 A | 8/1994 | Discko, Jr. | |
| 5,354,537 A | 10/1994 | Moreno | |
| 5,382,162 A * | 1/1995 | Sharp | 433/116 |
| 5,484,417 A | 1/1996 | Waitz et al. | |
| 5,489,207 A | 2/1996 | Dragan et al. | |
| 5,637,101 A | 6/1997 | Shillington | |
| 5,655,906 A * | 8/1997 | Coss et al. | 433/115 |
| 5,893,713 A | 4/1999 | Garman et al. | |
| 5,902,105 A | 5/1999 | Uejima et al. | |
| 5,934,903 A | 8/1999 | Marlin | |
| 6,018,860 A | 2/2000 | Smith et al. | |
| 6,056,165 A | 5/2000 | Speranza | |
| 6,095,811 A * | 8/2000 | Stearns | 433/29 |
| 6,106,283 A | 8/2000 | Roffe et al. | |
| 6,168,432 B1 | 1/2001 | Marlin | |
| 6,224,378 B1 * | 5/2001 | Valdes et al. | 433/224 |
| 6,270,343 B1 | 8/2001 | Martin | |
| 6,312,254 B1 | 11/2001 | Friedman | |
| 6,312,261 B1 * | 11/2001 | Mays | 433/224 |
| 6,319,002 B1 | 11/2001 | Pond | |
| 6,322,361 B1 * | 11/2001 | Esrock | 433/80 |
| 6,416,320 B1 | 7/2002 | Roffe et al. | |
| 6,443,729 B1 * | 9/2002 | Watson | 433/30 |
| 6,500,001 B2 | 12/2002 | Horth et al. | |
| 6,503,084 B2 | 1/2003 | Evers et al. | |
| 6,524,102 B2 | 2/2003 | Davis | |
| 6,572,589 B2 | 6/2003 | Tanaka et al. | |
| 6,616,448 B2 | 9/2003 | Friedman | |
| 6,981,868 B2 * | 1/2006 | Okawa et al. | 433/81 |
| 6,991,457 B2 | 1/2006 | Kazen et al. | |
| 7,008,222 B2 * | 3/2006 | Oh | 433/81 |
| 7,217,128 B2 * | 5/2007 | Atkin et al. | 433/119 |
| 2002/0058231 A1 | 5/2002 | Friedman | |
| 2002/0086264 A1 | 7/2002 | Okawa et al. | |
| 2004/0009452 A1 * | 1/2004 | Oh | 433/81 |
| 2004/0048226 A1 * | 3/2004 | Garman | 433/81 |
| 2004/0224282 A1 * | 11/2004 | Kazen et al. | 433/81 |
| 2004/0265772 A1 * | 12/2004 | Oh | 433/81 |
| 2005/0287490 A1 * | 12/2005 | Stookey et al. | 433/29 |

FOREIGN PATENT DOCUMENTS

| | | |
|---|---|---|
| EP | 0522239 A1 | 1/1993 |
| WO | 2004100821 A1 | 11/2004 |

OTHER PUBLICATIONS

European Patent Office, Invitation to Pay Additional Fees and Partial International Search Report, Jan. 24, 2006.

European Patent Office, Notification of Transmittal of the International Preliminary Report of Patentability, International Application No. PCT/US2005/033182, Oct. 17, 2006, 14 pgs.

* cited by examiner

MEDICAL TREATMENT APPARATUS

CROSS REFERENCES

This application claims the priority benefit of U.S. Provisional Patent Application Ser. No. 60/611,187, filed Sep. 17, 2004, the disclosure of which is hereby fully incorporated herein by reference.

FIELD OF THE INVENTION

The present invention relates generally to hand held medical treatment devices, and more particularly, to devices for treating root canal cavities.

BACKGROUND OF THE INVENTION

Various hand operated instruments exist for use by dentists, endodontists and other medical professionals. For example, during root canal procedures, dental pulp is removed in the area of the root canals and the dentist or endodontist obturates the tooth by filling the hollow, enlarged canals with a suitable filler material and then sealing the tooth. This prevents further infection of the tooth and/or surrounding area. Typically, the root canal is obturated by injecting gutta percha or other material in a softened and highly viscous condition. The gutta percha then hardens within the enlarged and cleaned root canals, while also retaining some resiliency. Usually root canal filler materials are thermoplastic in that they are initially solid or semi-solid and become softened and extrudable after heating. Various other types of materials may be extruded or otherwise dispensed during dental, endodontic or other medical procedures. Such instruments may or may not have disposable compules or cartridges of the material which may be inserted into the device, heated just prior to use, and disposed of after the treatment.

Various needs for improvement exists in the area of medical devices that are hand-operated and, even more particularly, in the area of hand-operated dental and/or endodontic instruments that dispense materials. Such needs include, for example, manners to improve the ability to easily allow for sterilization and reuse of the device on different patients, the ability to efficiently and uniformly preheat a disposable cartridge or compule of material, and the ability to efficiently manufacture an effective single-use needle or cannula associated with the single-use cartridge or compule of material. These and other areas of improvement are addressed by the present invention.

SUMMARY OF THE INVENTION

In one aspect, the invention provides an apparatus for dispensing a material during a dental or endodontic procedure. The apparatus generally comprises a housing including a motor with an output, a proximal end and a distal end extending along a longitudinal axis. A needle heating member, including a chamber, extends around the longitudinal axis proximate the distal end. An opening in the housing at the distal end extends around the longitudinal axis. The opening communicates with the chamber and is configured to receive a disposable needle prefilled with the material. A plunger or piston is coupled with the motor and is configured to expel the material from the needle during activation of the motor. A heater at least substantially surrounds the chamber for heating the material in the needle.

Various additional aspects include the provision of a removable, autoclavable sheath for surrounding the housing. The sheath may be comprised of a first member and a second member with the first member being longer than the second member and more rigid than the second member. The second member is positioned at and covers at least a portion of the distal end of the housing. This, for example, can help seal the housing. In addition, the second member may be formed from a resilient and/or heat insulative material to provide comfort and protection to both the user and the patient.

In another aspect of the invention, a heat conductive support piece is in thermal contact with a needle heating member associated with the chamber. The heat conductive support piece provides a heat sink to store heat energy and, upon initial insertion of the needle, transfer the heat energy to the material in the needle. The heat conductive support piece is therefore designed to avoid dissipating heat to the environment or air space surrounding the support piece and instead retains the heat for use in assisting with heating the material in the needle. The heat conductive support piece may be formed from a heat conductive, nonmetallic material, or any other material of known, relatively high heat conductivity. The support piece may make intermittent contact or full contact with the internal wall surfaces of the housing.

In another aspect, a reusable protective sheath is provided and capable of being attached to and removed from a hand-operated medical instrument. The sheath generally comprises a rigid body portion having a generally tubular, elongate shape with proximal and distal ends and having at least one connector portion for releasably connecting the body portion to the hand-operated medical instrument. This connector portion may, for example, simply be a friction fit or may comprise an actual mechanical connector or fastener of any suitable type. An outer boot portion is coupled to at least the distal end of the body portion and extends toward the proximal end. The outer boot portion surrounds the rigid body portion and is formed from a material more resilient than the body portion. This outer boot portion may be formed from a separate piece which is then affixed, for example, by friction to the rigid body portion, or may be formed onto the body portion during a manufacturing operation, such as by a molding operation.

The invention further contemplates a method of manufacturing a needle for use in dispensing a material during a dental or endodontic procedure. The method generally comprises drawing a blank of metal into a tubular element having an opened proximal end and a closed distal end extending along a first axis. The blank is bent during a bending operation such that a proximal portion of the blank extends along the first axis and a distal portion of the blank extends along a different, second axis oriented at an acute angle relative to the first axis. A portion of the drawn metal is removed from the distal end to open the distal end thereby forming the needle capable of dispensing the material through the open distal end.

Various additional objectives, advantages and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION OF THE ILLUSTRATIVE EMBODIMENTS

Figure 1:
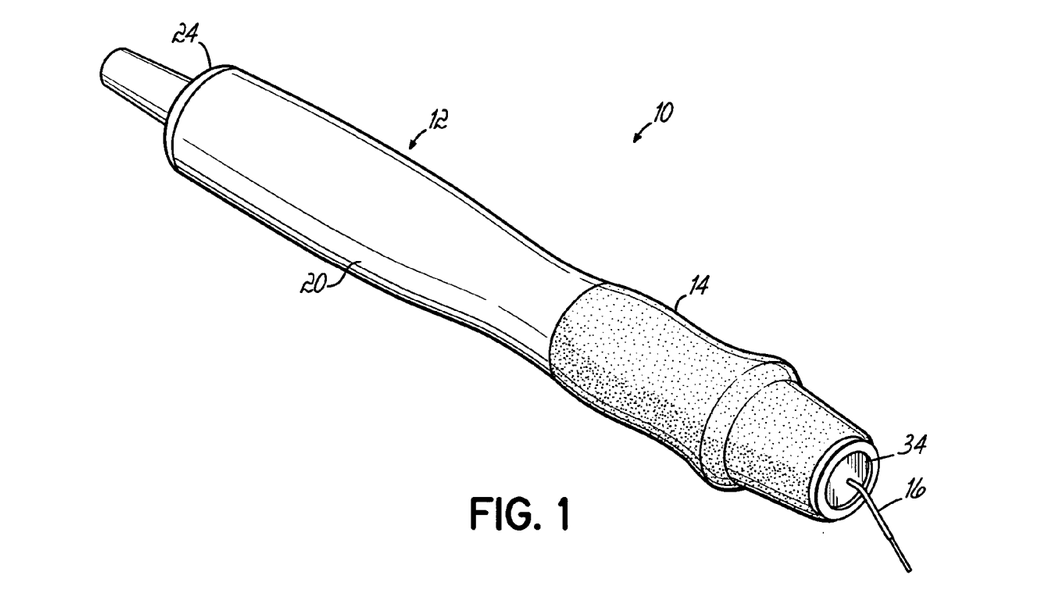
FIG. 1 is a perspective view of a dental treatment apparatus according to a first embodiment of the present invention.

With reference to FIG. 1, a dental treatment apparatus 10 for dispensing a material, such as a thermoplastic filler material, includes a hand piece 12, barrier 14, and needle 16. The barrier 14 and needle 16 may be removably coupled to the hand piece 12 for sterilization purposes, as will be discussed in greater detail below. Also, although the apparatus 10 will be described in connection with the treatment of root canals, those having ordinary skill in the art will recognize that the present invention may equally apply to other types of dental, endodontic or other medical treatment equipment.

Figure 2:
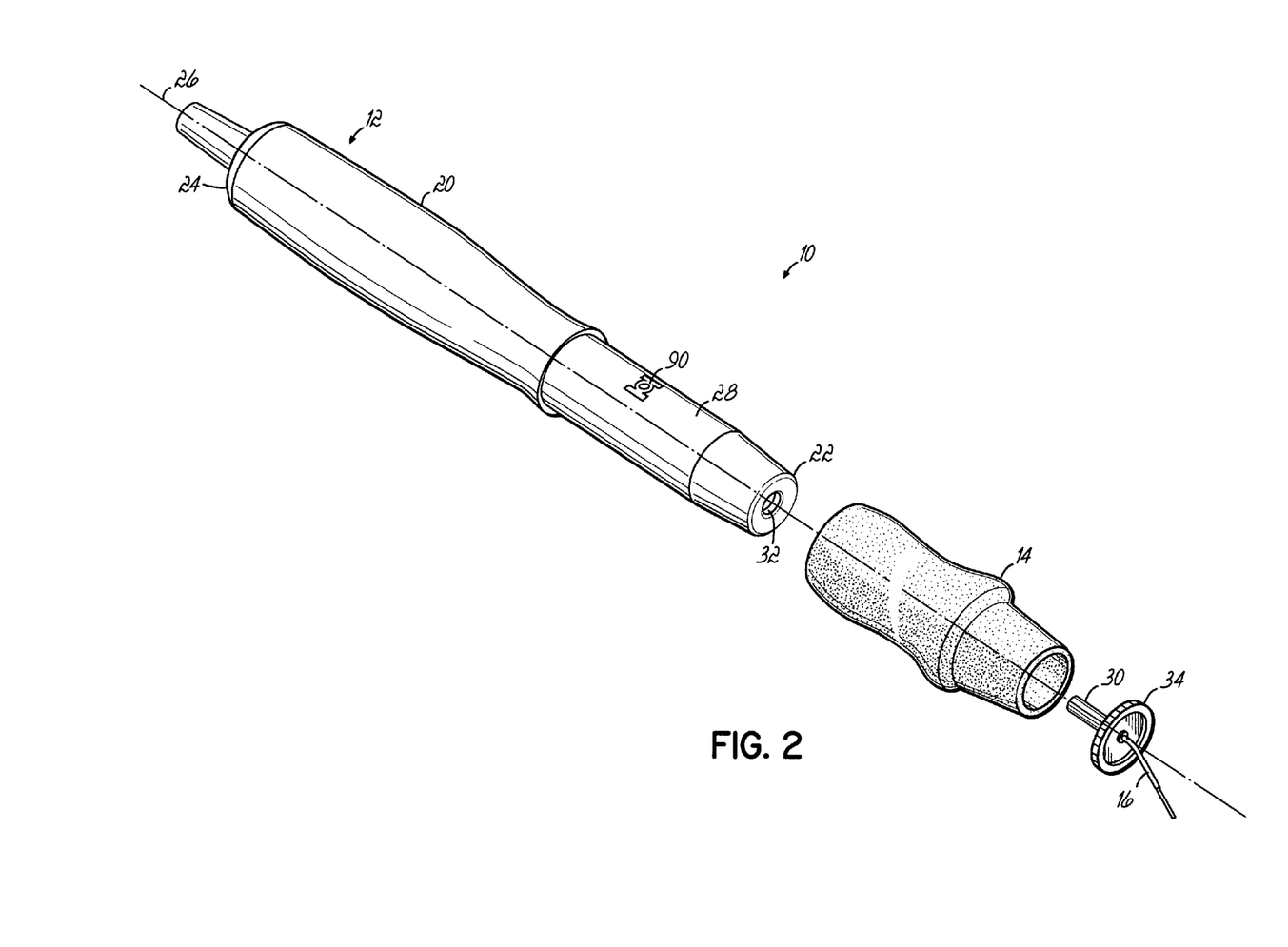
FIG. 2 is an exploded perspective view similar to FIG. 1.
Figure 3:
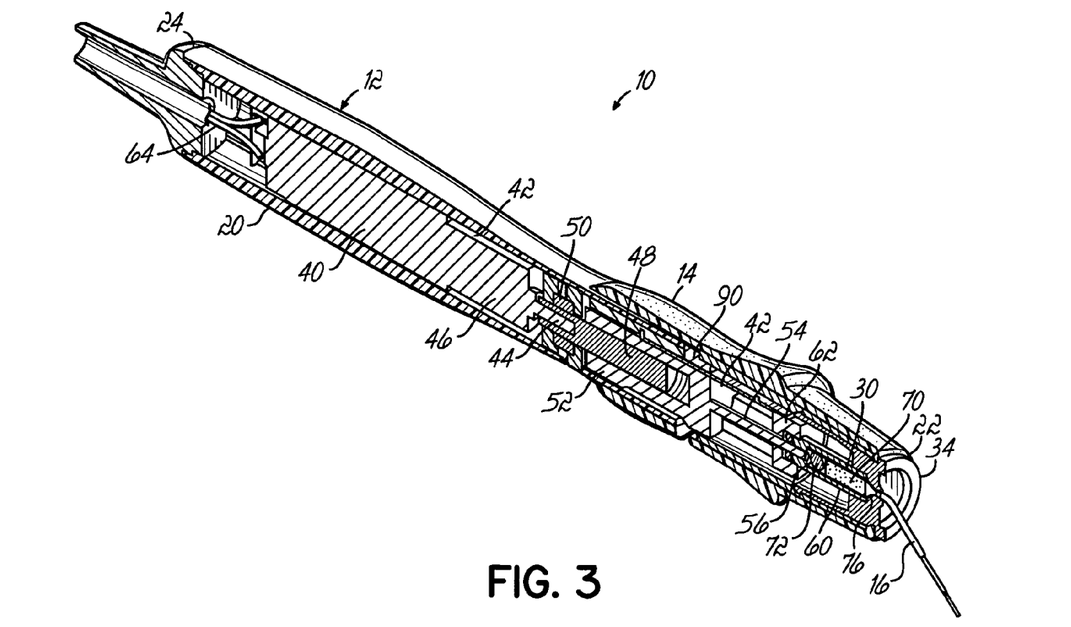
FIG. 3 is a cross sectional view along the longitudinal central axis of the apparatus shown in FIG. 1.

As shown in FIGS. 2 and 3, the hand piece 12 is comprised of a housing 20 having front (distal) and rear (proximal) ends 22, 24 and a longitudinal axis 26. The housing 20 may be generally cylindrical in nature, with the barrier 14 slidably mounted over a front portion 28. In one embodiment, the front portion 28 may have a reduced diameter so that the outer surface of the barrier 14 is flush with the outer surface of the housing 20. Also, both the housing 20 and barrier 14 may have curved profiles that are designed to optimize the ergonomic comfort and ease of use for a dentist. The hand piece 12 may also receive a proximal portion 30 of a dispensing needle 16, which is inserted into an aperture 32 on the front end 22. A removable end cap 34 which may have a snap fit within housing 20, or be threaded or otherwise secured to front end 22 seals the aperture 32 and secures the needle 16 within the housing 20.

Referring more specifically to FIGS. 2 and 3, a variable speed electric motor 40 is mounted within an internal cavity 42 that is defined by the housing 20. The motor 40 includes an output shaft 44 and, if necessary, a gear reducer 46. The output shaft 44 is connected to a lead screw 48, which is supported within the cavity 42 by a bearing member 50. Output shaft 44 and lead screw 48 are rotating components and rotation of lead screw 48 is translated into movement of an internally threaded plunger 52 along the longitudinal axis 26. A plunger end 54 extends along the longitudinal axis 26 as well, and is received in a proximal end 56 of the needle portion 30.

Still referring to FIG. 3, the housing 20 further includes a heating element 60 that surrounds the needle portion 30 and a support piece 62 positioned proximate to the heating element 60. The motor 40 and heating element 60 may be coupled to an electronic control (not shown), which may be separate from the hand piece 12 or incorporated thereon. If separate, the necessary communication between the control and hand piece 12 may be accomplished by lead wires 64 extending from the rear or proximal end 24. Note that the lead wires 64 may also be used to supply power to the motor 40 from an external power source (not shown).

Figure 4:
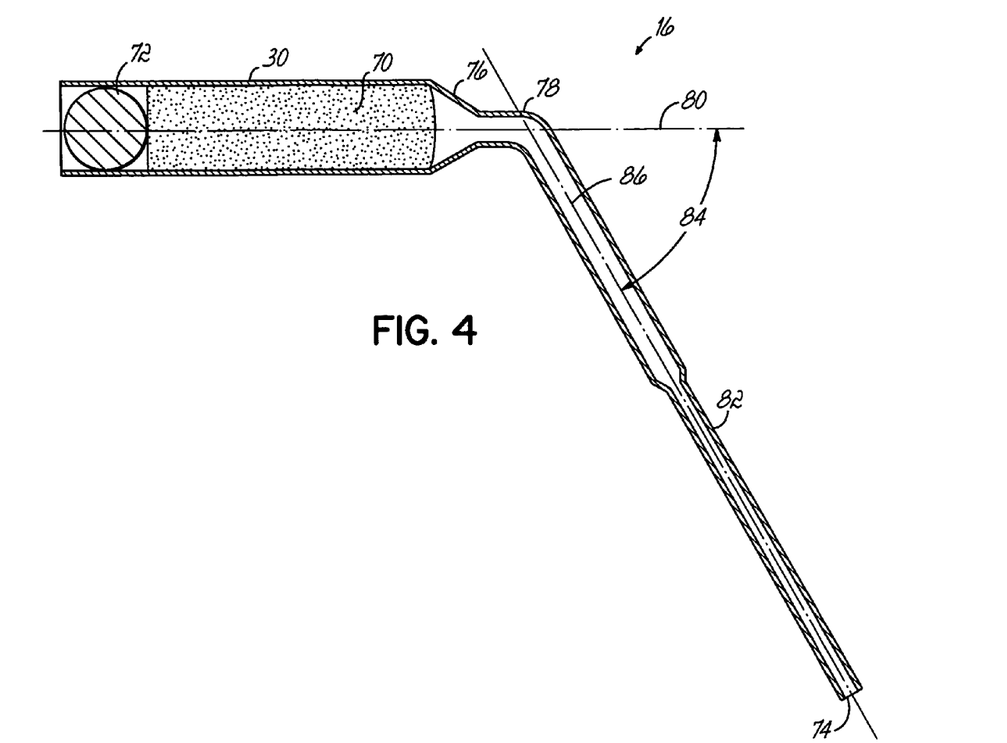
FIG. 4 is a cross sectional side view of a needle used in the dental treatment apparatus of FIG. 1.

With reference to FIG. 4, a detailed drawing of the needle 16 is shown. As shown in the figure, the needle 16 is of tubular construction and includes the proximal portion comprising a compule or cartridge 30, which contains gutta percha 70 to be dispensed, as well as a proximally located seal in the form of a ball 72, which serves as a piston for extruding the gutta percha (or other filling material) 70 through an open distal end 74 of the needle 16. At the front end of the proximal portion 30, a frustoconical shoulder 76 leads to a reduced diameter first needle portion 78. The frustoconical shoulder 76 helps to hold the needle 16 in the housing 20. The proximal portion 30, frustoconical shoulder 76, and first needle portion 78 all extend along a single axis 80. One or more reduced diameter needle portions 82 are located distal to needle portion 78. Due to a bend or angle 84, the needle portion(s) 82 extend along an entirely different axis 86 relative to the proximal portion 30, frustoconical shoulder 76 and first needle portion 78 which extend along axis 80. As a result, the needle 16 itself does not extend along a single longitudinal axis, but rather along combined axes 80 and 86.

Regarding the method of manufacturing needle 16, a blank will be drawn from a flat plate of material, such as silver, such that it extends along a single axis, and has a hollow interior with a closed distal end. In this form, the blank would not function as a needle since it would not dispense material due to the closed distal end. Once drawn, the blank is bent to a predetermined angle, such as the 60° (+5°/−35°) as shown in FIG. 4. After bending the blank, the closed end is cut off using circular or V-shearing dies to form needle 16. Gutta percha or another filling material is then inserted into the larger diameter proximal portion 30, followed by insertion of the piston ball 72 to complete the manufacturing process. The piston ball 72 should be formed from a material that has a greater coefficient of thermal expansion than the proximal needle portion 30. For example, the piston ball 72 may be formed from silicon rubber.

In use, the end cap 34 is removed from the housing 20 so that the proximal portion 30 of the needle 16 may be inserted into the cavity 42 and properly positioned along the longitudinal axis 26. Thus, the axis 80 of needle 16 will generally be aligned with the longitudinal axis 26 of hand piece 12. After replacing the end cap 34 and sliding the barrier 14 over the housing 20, the heating element 60 may be activated to raise the temperature of the gutta percha material 70. The present invention further contemplates several advantageous features to avoid unnecessary heating. For example, a sensor (not shown) may be positioned within the housing 20 to determine if the needle 16 has been inserted. If the needle 16 is not present, the heating element 60 will not operate. The display associated with the hand piece 12 will also indicate that the needle 16 is not in place. Second, the heating element 60 may be programmed to automatically shut off after a predetermined amount of time. Such a feature helps prevent the degradation of the gutta percha material 70 by protecting it from prolonged exposure to elevated temperatures. Third, the heating element 60 may be disabled to allow for room temperature extrusion or dispensing of materials other than gutta percha.

Once the gutta percha 70 has been heated to the appropriate temperature for extrusion, which may be approximately 200° C., the user may grip the apparatus 10 in the manner of a pen and activate the extrusion motor 40 by pressing a button 90 (FIG. 2) on the housing 20. Note that the barrier 14 should be configured to allow a user to operate the button 90 even though it may slide over the button 90. For example, at least the portion of the barrier 14 directly above the push button 90 may be resilient. The entire barrier may be resilient instead, such as by forming it from a material such as silicone rubber. Further note that a temperature sensor and appropriate control circuitry may be used to prevent motor operation until a desired temperature is reached, thereby assuring that the gutta percha 70 has softened sufficiently for extrusion from the needle 16.

The operation of the motor 40 causes the lead screw 48 to rotate within plunger 52. This causes plunger 52 to travel along the longitudinal axis 26. As the plunger 52 moves towards the front end 22, the plunger end 54 contacts the piston ball 72 and forces the gutta percha 70 out of the needle 16. At any point during operation, the user may release the button 90 to stop the extrusion of the gutta percha 70. Furthermore, the control circuitry of the apparatus 10 may be programmed to cause the plunger end 54 to back up slightly to help prevent any further extrusion once the button 90 has been released.

Once the operation or extrusion process has been completed, the motor 40 may be set to rotate in a reverse direction to rotate the lead screw 48 in an opposite direction and thereby retract plunger 52 and end 54. The end cap 34 may then be removed and the needle 16 may be discarded and replaced with a new needle 16, prefilled with material. Because the gutta percha 70 is pre-loaded into the disposable needle 16, the need to remove residual gutta percha material from the hand piece 12 is eliminated. Furthermore, significant benefits are realized from the construction of the needle 16, as well as from its method of manufacture. Relative to the construction, the angle 84 allows easier access to the interior of a patient's tooth during use. Since the needle 16 is pre-bent, there is less likelihood that a dental professional will kink or otherwise damage the needle 16 while attempting to bend the needle 16 to suit a particular patient. Relative to the method of manufacture, leaving the end of the drawn blank closed during the bending operation helps to ensure that the distal end 74 is not crushed during the bending operation. This is due to the fact that the closed end imparts significant added strength to the distal end 74 in the cross-sectional direction.

Figure 5:
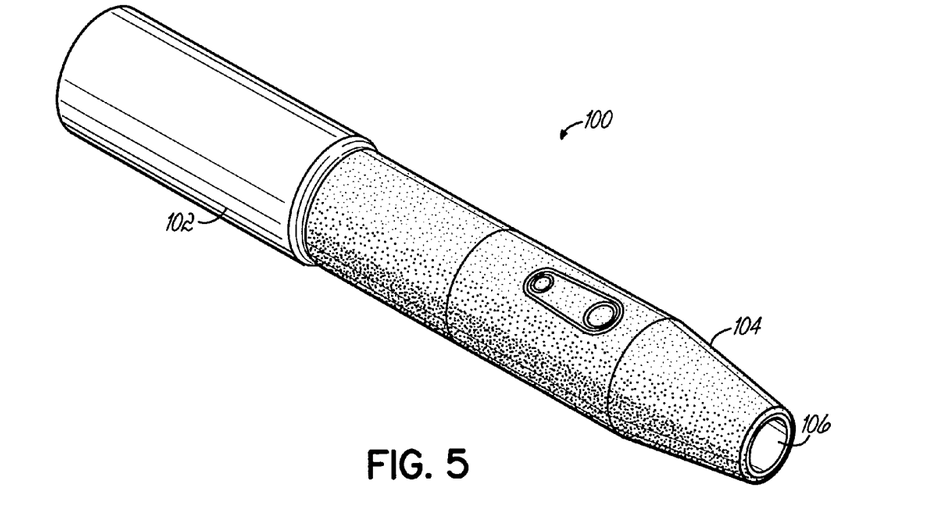
FIG. 5 is a perspective view of a sheath used on a dental treatment apparatus according to a second embodiment of the present invention.
Figure 6:
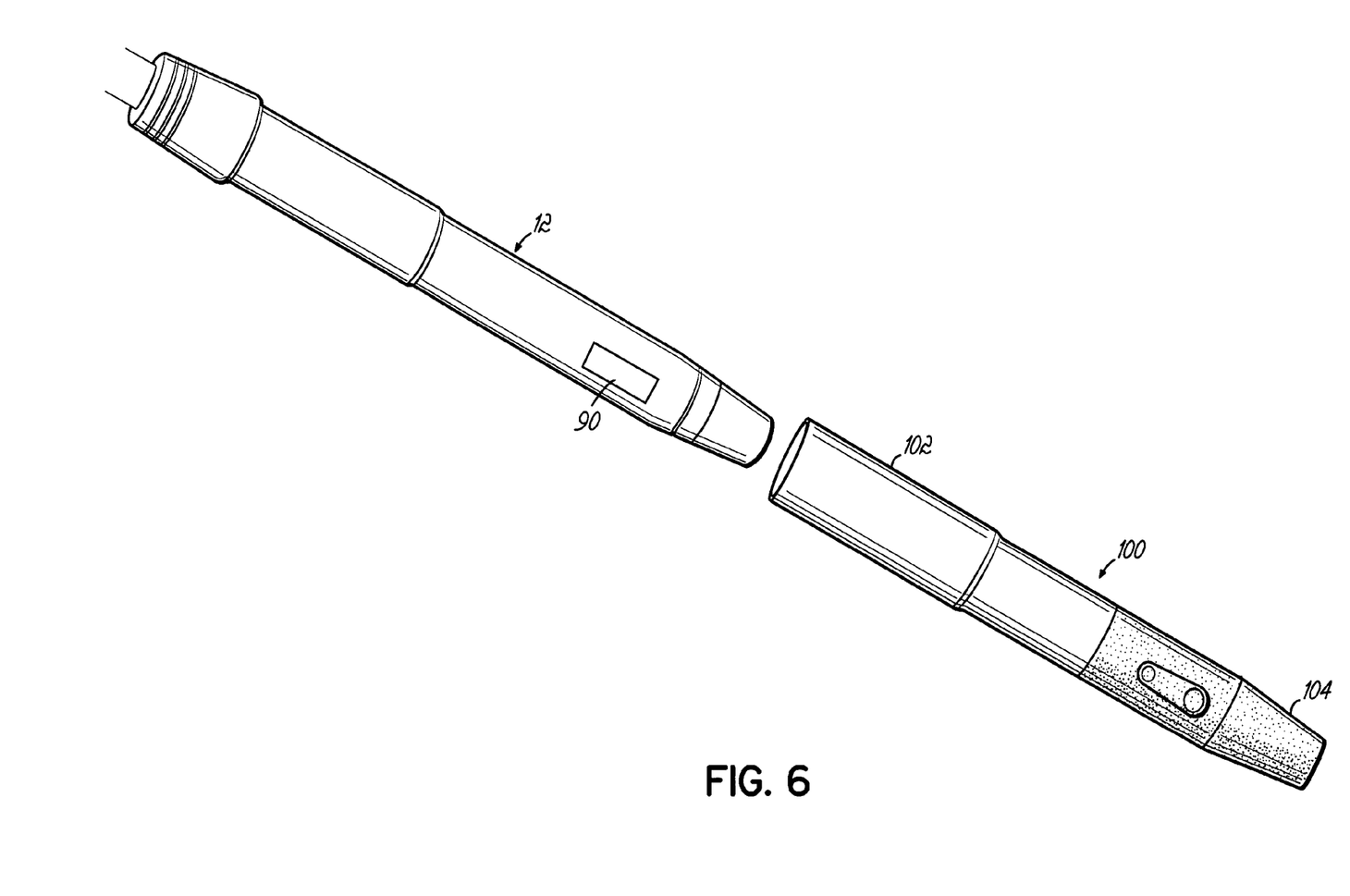
FIG. 6 is an exploded perspective view of a dental treatment apparatus according to a second embodiment of the present invention.

Before loading a new needle for a second operation, the hand piece 12 must be sterilized to avoid cross-contamination between patients. Because sterilization processes, such as autoclaving, can take significant amounts of time, a second embodiment of the present invention includes a reusable sheath 100, as shown in FIGS. 5 and 6. Like reference numbers are used in the figures to indicate like elements from the first embodiment discussed above.

Unlike the barrier 14, the sheath 100 includes a body portion 102 that is designed to closely follow the contours of a substantial portion of the hand piece 12. The body portion 102 is removably coupled to the hand piece 12 and may be formed from a metal or plastic material capable of repeated autoclave cycling. Alternatively, sheath 100 may be a single-use disposable sheath. The sheath 100 also includes a flexible seal portion 104 designed to provide an effective seal around an orifice 106, which may receive needles or other components necessary for medical treatment. For example, body portion 102 may be an aluminum sheath that extends along at least substantially the entire length of the hand piece 12 and has a snap fit, friction fit or other easily accomplished manner of connection and disconnection with the hand piece 12. The flexible seal portion 104 may be formed as a resilient generally cylindrically shaped boot that is retained on a distal portion of the body portion 102 by friction. The boot may, for example, be formed of silicone rubber. In this way, the boot performs a sealing function at the distal end of the hand piece and provides a thermal shield to prevent hot surfaces of the hand piece from contacting the patient during treatment. Because both the body portion 102 and seal portion 104 are made from autoclavable or disposable materials, a user can purchase multiple sheaths for a particular hand piece and keep clean units ready for use, thereby avoiding sterilization downtime between patients.

Figure 7:
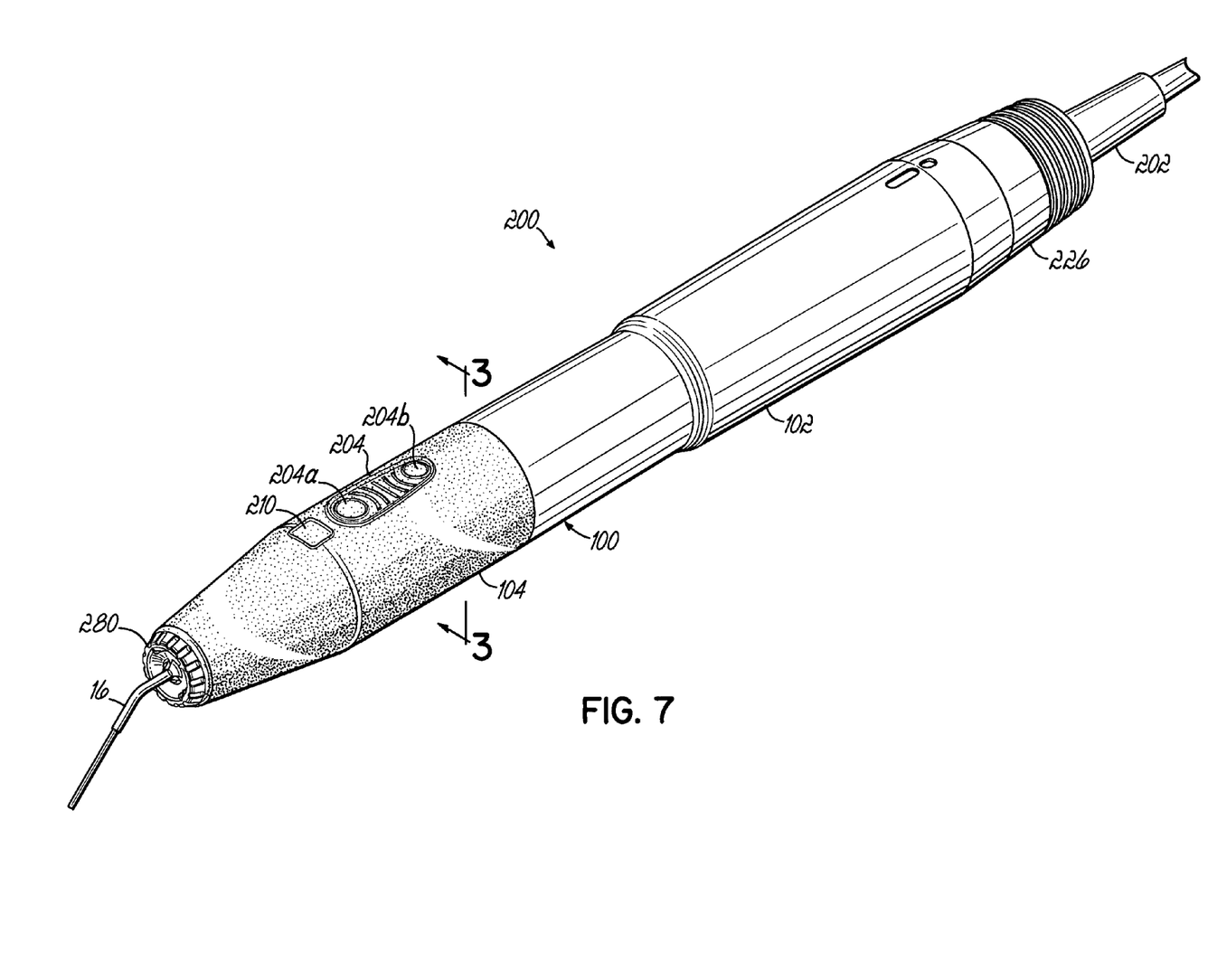
FIG. 7 is a perspective view of another embodiment of a hand-operated medical treatment apparatus in the form of an obturation device.

In FIGS. 7-13, like reference numerals are used to refer to like components of the previously described embodiments. FIG. 7 illustrates another embodiment of a hand piece 200, and specifically a hand operated obturation device. Like the previous embodiment, this device 200 may be conveniently and easily held and operated by one hand in a manner similar to handling a writing instrument, such as a pen. The principles of the invention disclosed in this second embodiment may likewise apply to other medical treatment apparatus. A proximal end of the device receives an electrical cord set 202 from a console unit (not shown) for power and control purposes, and a distal end of the device holds an integral cartridge and needle 16, as previously described. A generally cylindrical, sterilizable sheath 100, as described above, covers the outside of the device and is removably attached via a friction fit or snap fit using, for example, an O-ring 101 secured around the housing. This sheath 100 may also be formed by an aluminum body portion 102 covered at a distal end by a silicone sealing boot 104. The silicone boot 104 has a switch area 204 that comprises two "push buttons" or raised portions 204a, 204b for operating two separate switches, defining two different speeds of the device, as will be described below. These push buttons 204a, 204b can extend through a window (not shown in FIG. 7) in the underlying aluminum body 102 such that the push buttons 204a, 204b may contact separate switches mounted within the device 200. A window 210 is provided for viewing a pair of LED indicator lights 212, 214 (see FIG. 10A) for communicating to the user whether the device 200 is operating under a high speed or a low speed.

Figure 8:
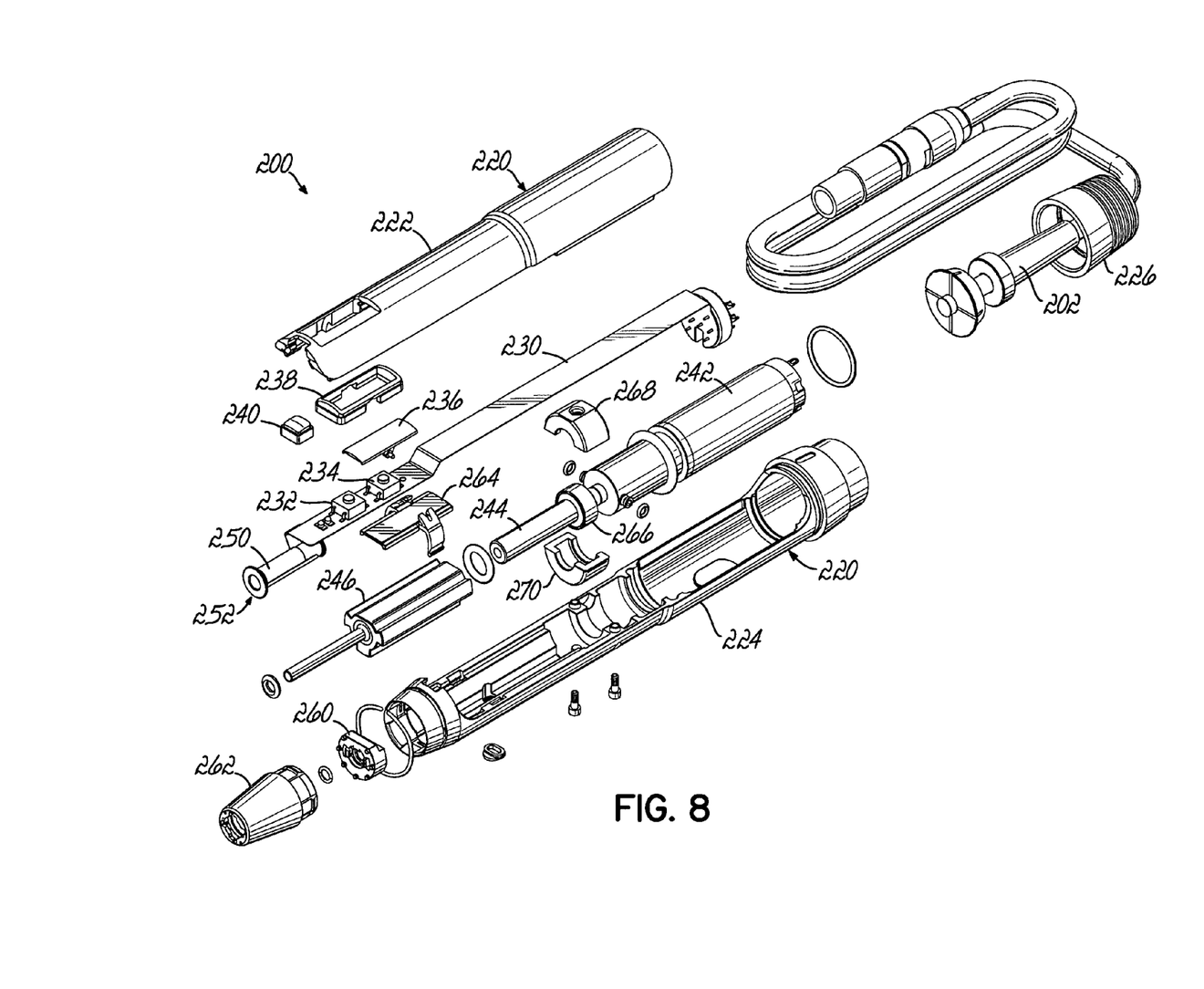
FIG. 8 is an exploded perspective view of various main components of the obturation device shown in FIG. 7.

Referring to FIG. 8, various major components of the device 200 are shown in exploded form. The various components are generally received and mounted within a housing 220 having an upper housing portion 222 and a lower housing 224 portion which may, for example, be formed from metal, such as an aluminum casting. Cord set 202 extends through a proximal end cap 226 and provides electrical power (through leads, not shown in FIG. 8) for the various electromotive and control components of the device 200. A circuit board 230 is provided for control purposes and includes the pair of previously mentioned switches 232, 234 operated by a switch rocker 236 surrounded by a switch frame 238. The pair of previously mentioned LED indicator lights 212, 214 are viewable through a window 240. The switches 232, 234 operate a motor 242 that rotates a lead screw 244 to operate a plunger 246 in a reciprocating fashion for purposes to be described below. The motor 242 may be operated in both a high speed and a low speed by selectively depressing either the high speed switch 232 or the low speed switch 234. The circuit board 230 has an integrated heating element 250 that is wrapped at least substantially completely around and along at least substantially the entire length of a generally cylindrical heater and sensor assembly 252 that receives the proximal or cartridge end of the needle 16. The heater and sensor assembly 252 may be supported on a proximal end thereof by a suitable support piece 260 which abuts against a proximal end of a distal cap 262. The distal cap 262 clips into a distal end of the lower housing portion 224. The switches 232, 234 are supported from below by a switch bracket 264 coupled to the lower housing portion 224. The lead screw 244 is supported by a bearing 266 for rotation, and the bearing is supported by a pair of cooperating bearing supports 268, 270 affixed to the housing 220.

Figure 9:
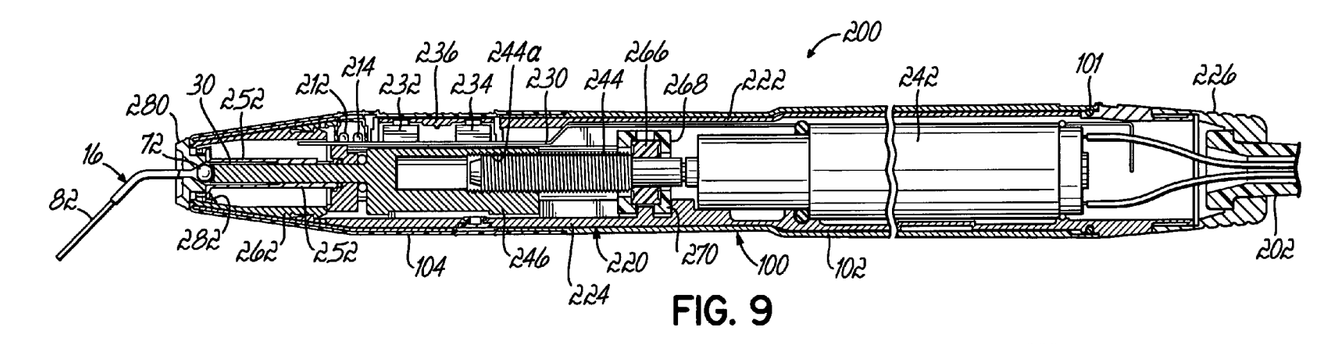
FIG. 9 is a cross sectional view taken along the longitudinal axis of the obturation device shown in FIG. 7.
Figure 10A:
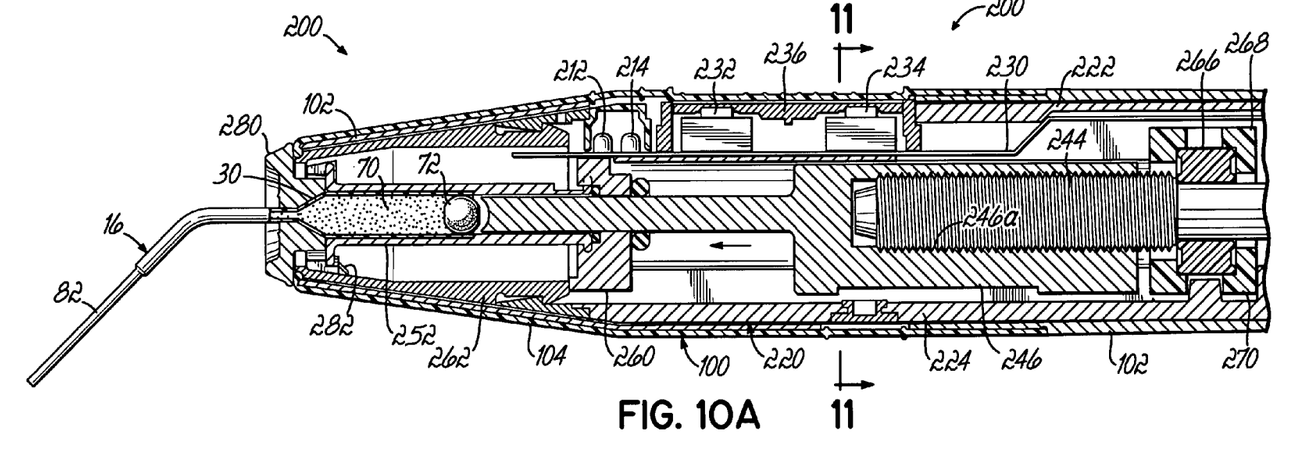
FIG. 10A is an enlarged view of the distal end of the device shown in FIG. 9.
Figure 10B:
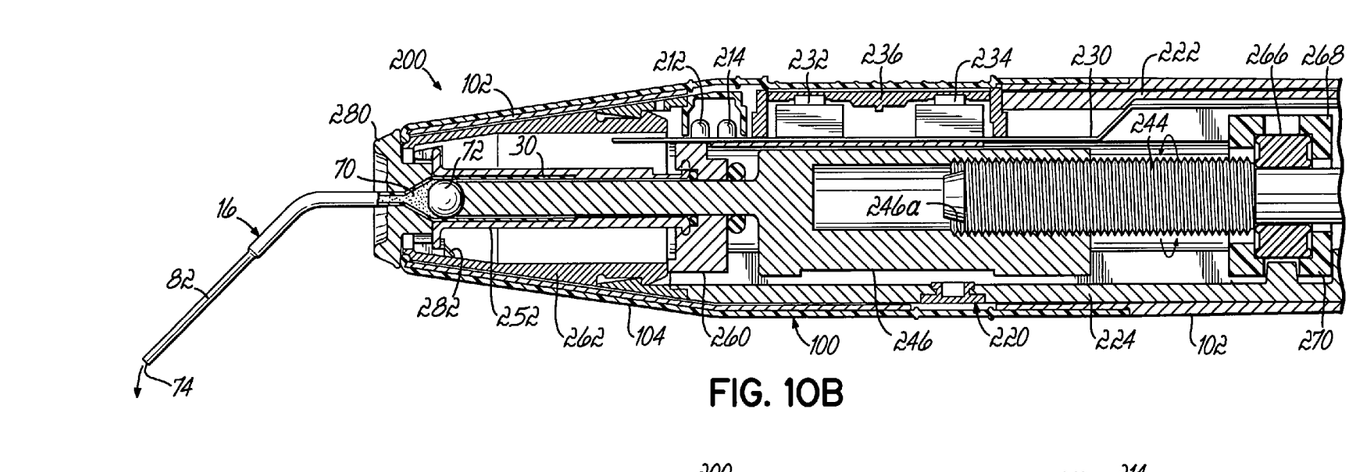
FIG. 10B is a cross sectional view similar to FIG. 10A, but illustrating the plunger extended during an extrusion operation.
Figure 10C:
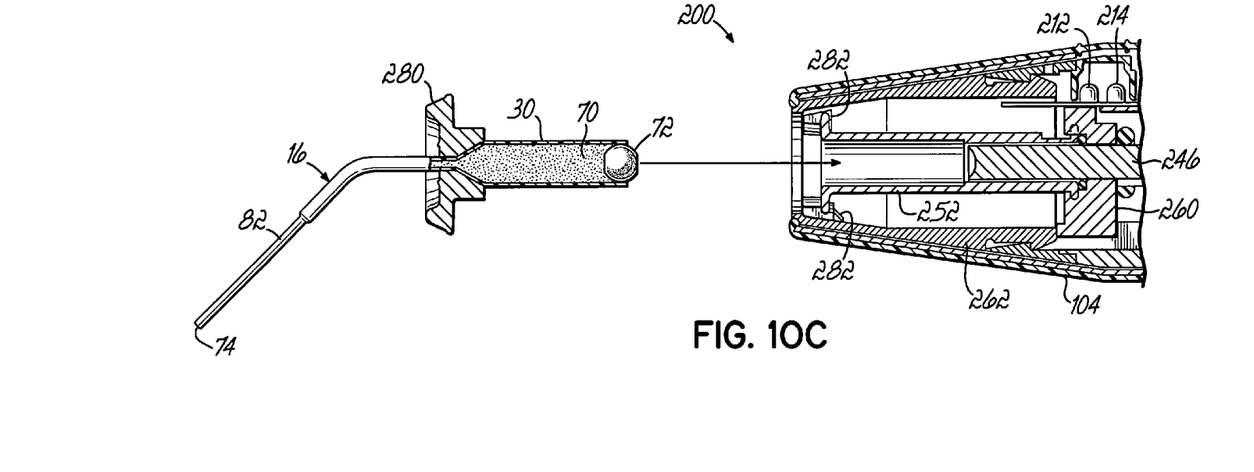
FIG. 10C is an exploded cross sectional view similar to FIGS. 10A and 10B, but illustrating the insertion of the disposable cartridge or compule of dental filler material, such as gutta percha, as well as the associated needle or cannula for dispensing purposes.

Referring now to FIGS. 9, 10A and 10B, the obturation device 200 is operated by activating the motor 242 to rotate the lead screw 244 within a threaded portion 246a of the plunger 246. The interaction of the external threads of the lead screw 244 and the internal threads 246a of the plunger 246 results in reciprocating motion of the plunger 246 back and forth depending on the direction of rotation of the lead screw 244. It will be appreciated that a reverse switch should be provided to allow retraction of plunger 246, at least after a treatment has been completed. This reverse switch may be located on the device or handpiece 200 itself or on a control console (not shown) associated with the device 200. As shown best in FIG. 11, the plunger 246 includes a generally triangular shaped body portion 274 defining slide members 274a, 274b, 274c that are received within corresponding grooves 276a, 276b, 276c within the housing 220 to allow and guide reciprocating, sliding motion of the plunger 246 in a direction parallel to the longitudinal axis of the device 200. As shown in FIG. 10C, the proximal end of the needle 16 is inserted through the distal end of the device 200 and into a cylindrical chamber of the heater and temperature sensor assembly 252. A connector 280 associated with the distal end of the device 200 holds the needle 16 in place within the cap 262 with a bayonet style connection. The proximal cartridge or compule portion of the needle 16 may contain any desired material for extrusion purposes, such as gutta percha, and includes a piston ball 72 within a proximal open end portion thereof. The ball 72 is contacted by the distal end or tip of the plunger 246 which has a generally complimentary shape, with the ball 72 being convex and the distal end of the plunger 246 being concave. FIG. 10A shows the relative position of the piston ball and plunger 246 prior to activation of the device 200 to extrude the material, and FIG. 10B illustrates rotation of the lead screw 244 and resulting reciprocating motion of the plunger 246 into the cartridge or compule portion of the needle 16 to move the ball 72 and thereby extrude the material from the open distal end of the needle 16.

The support piece 260 at the proximal end of the heater and temperature sensor assembly 252 may take on various forms. In one embodiment, it may comprise a thermally insulative plastic piece, such as a thermally insulative form of Ultem™ available from General Electric, or any other known suitable insulative material. Other embodiments are advantageously formed of heat conductive plastic, metal or any other heat conductive material. Suitable heat conductive plastics or composites may include, for example, CoolPoly E Series plastics, available from Cool Polymers, Inc. and Konduit, available from General Electric. For example, the material of piece 260 has a thermal conductivity of at least about 40 W/mK. Support piece 260 may also transfer heat to the housing 220 since the sheath 100 is spaced from the housing 220 and therefore provides a thermal shield to the user. Heat conductive materials such as these are available in various base resins Polypropylene (PP), Polyphenylene Sulfide (PPS), liquid crystal polymers (LCP), nylon (PA), Polybutylene Terephthalate (PBT) and PEI (Ultem based). Different thermally conductive fillers (such as ceramics, carbon fiber, graphite, etc.) provide the desired thermal conductivity. Such heat conductive materials would, for example, provide a heat sink for storing thermal energy which, upon insertion of a new, needle 16 filled with material at room temperature, transfer the stored heat energy to the cooler needle 16 and material therein. The support piece 260 is designed to have supportive multi-point contact with the surrounding inner walls of the housing 220 or associated structure and would therefore transfer some heat to the housing 220, especially if the housing 220 were formed from metal such as an aluminum casting. Much of the stored heat energy would, however, be stored in the support piece 260 and available for transfer into the needle 16. This feature allows for faster initial heating of the inserted needle upon start up. Another embodiment of a heat conductive support member is described below in connection with FIG. 12. Additional structure 282 supports the distal end of the heater and temperature sensor assembly 252 such that the inner chamber holding the compule or cartridge portion of the needle 16 extends along the central longitudinal axis of the device 200.

Figures 11, 12:
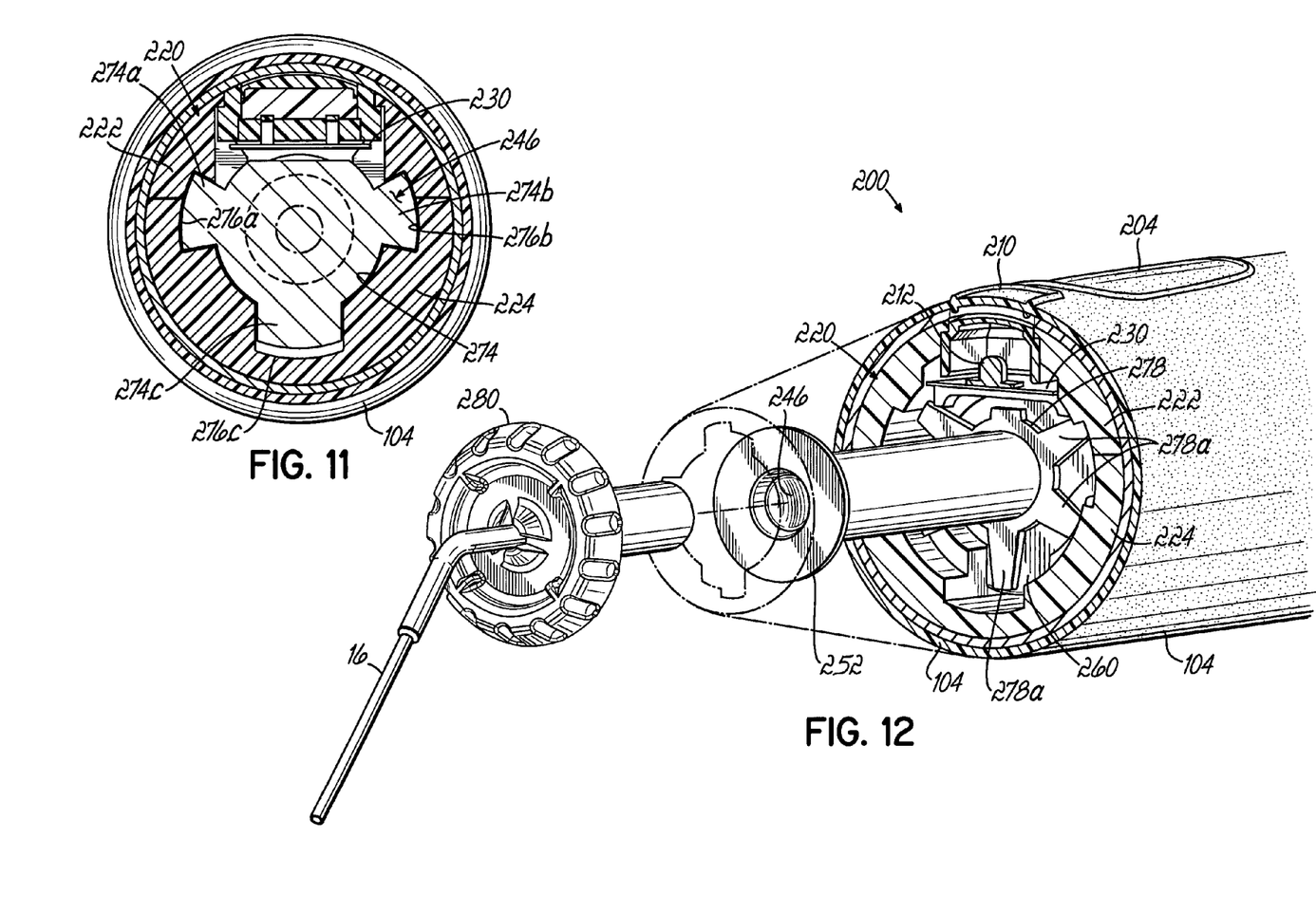
FIG. 11 is a cross sectional view taken along line 11-11 of FIG. 10B.
FIG. 12 is a perspective view illustrating the distal end of the device and showing an alternative embodiment with a heat sink support piece in contact with the heater associated with the obturation device.

FIG. 12 illustrates an alternative heat sink support structure in the form of a star-shaped support piece 278 having a plurality of radially extending legs 278a for establishing supportive contact with the inner walls of the housing 220 or other associated internal structure. Support piece may be formed from stainless steel, as is the heater assembly 252, or any other heat conductive material. Support piece 278 may be formed integrally with the heater assembly 252 as a proximal flange, or may be separately coupled to the proximal end of the heater assembly 252, such as through a press fit operation. Some heat will be conducted to the walls of the housing 220, while additional heat energy will be stored for a period of time in the support piece 278 such that it may be transferred into a new needle 16 inserted into the chamber of the heater assembly 252 as described above.

Figure 13:
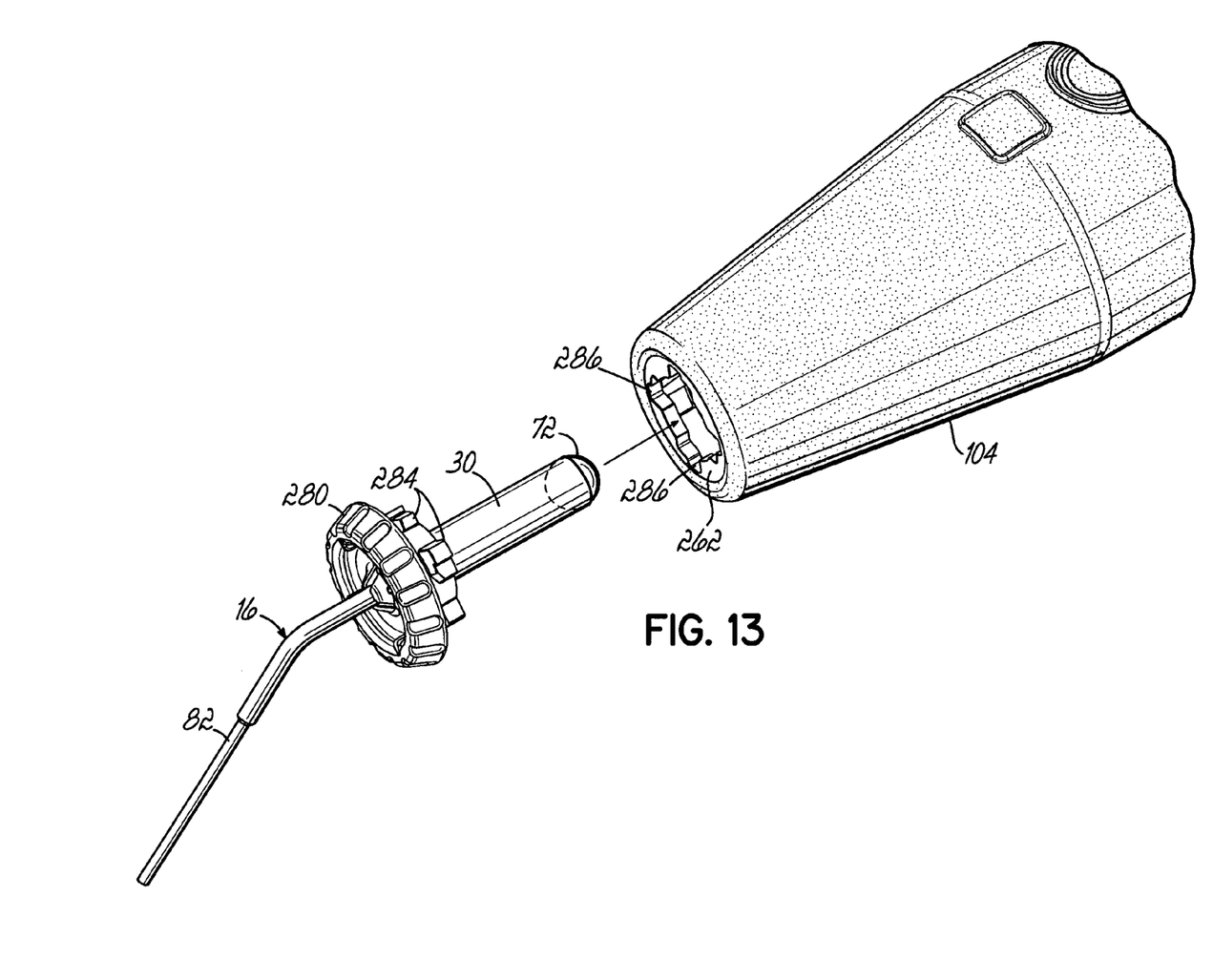
FIG. 13 is an exploded perspective view of the distal end of the device illustrating the insertion of the disposable compule or cartridge assembly.

FIG. 13 illustrates, in greater detail, the construction of the connector 280 that couples the needle 16 within the distal end of the device 200. As illustrated, the connector 280 has several projections 284 that mate with a corresponding number of recesses 286 within the distal end of the distal end cap 262 in such a manner that insertion of the connector 280 into the distal end cap 262 and rotation through a selected or predetermined angle will result in secure connection of the needle 16 within the heater and temperature sensor assembly 252, as previously described.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described.

Accordingly, departures may be made from such details without departing from the scope or spirit of the general inventive concept.

What is claimed is:

1. An apparatus for dispensing a material during a dental or endodontic procedure, comprising:
   a housing including a motor with an output, said housing further including a proximal end and a distal end extending along a longitudinal axis,
   a needle heating member including a chamber extending around the longitudinal axis proximate the distal end,
   an opening in said housing at the distal end extending around the longitudinal axis, said opening communicating with said chamber and configured to receive a disposable needle prefilled with the material,
   a plunger coupled with said motor and configured to expel the material from the needle during activation of said motor,
   a heating element thermally coupled with said needle heating member and at least substantially surrounding said chamber for heating the material in the needle, and
   a removable, autoclavable sheath surrounding at least a portion of said housing, said sheath comprising a first, rigid member and a second, resilient member at least partially overlying said first, rigid member and adapted to be gripped by a user while dispensing the material, said second, resilient member including an orifice configured to accommodate the disposable needle and a flexible seal portion configured to provide a seal around said orifice.

2. The apparatus of claim 1, wherein said second, resilient member completely surrounds said first, rigid member.

3. The apparatus of claim 1, further comprising a heat conductive support piece in thermal contact with said needle heating member, said heat conductive support piece member providing a heat sink to store heat energy and, upon initial insertion of the needle, transfer the heat energy to the material in the needle.

4. The apparatus of claim 3, wherein said support piece is formed from a heat conductive, non-metallic material.

5. The apparatus of claim 1, further comprising a removable end cap adapted to surround the needle and close said opening while retaining the needle within said chamber.

6. An apparatus for dispensing a material during a dental or endodontic procedure, comprising:
   a housing including a motor with an output, said housing further including a proximal end and a distal end extending along a longitudinal axis,
   a needle heating member including a chamber extending around the longitudinal axis proximate the distal end,
   an opening in said housing at the distal end extending around the longitudinal axis, said opening communicating with said chamber and configured to receive a disposable needle prefilled with the material,
   a plunger coupled with said motor and configured to expel the material from the needle during activation of said motor,
   a heating element thermally coupled with said needle heating member and at least substantially surrounding said chamber for heating the material in the needle, and
   a removable, autoclavable sheath surrounding at least a portion of said housing, said sheath comprising a first, rigid member and a second, resilient member at least partially overlying said first, rigid member and adapted to be gripped by a user while dispensing the material, wherein said first, rigid member is longer than said second, resilient member.

7. An apparatus for dispensing a material during a dental or endodontic procedure, comprising:
   a housing including a proximal end, a distal end, and a motor with an output;
   a needle heating member including a chamber extending around the longitudinal axis proximate the distal end;
   an opening in said housing at the distal end extending around the longitudinal axis, said opening communicating with said chamber and configured to receive a disposable needle prefilled with the material;
   a plunger drive assembly coupled with said motor and configured to expel the material from the needle during activation of said motor;
   a heating element thermally coupled with said needle heating member and at least substantially surrounding said chamber for heating the material in the needle;
   a heat conductive support piece in thermal contact with said needle heating member, said heat conductive support piece providing a heat sink to store heat energy and, upon initial insertion of the needle, transfer the heat energy to the material in the needle; and
   wherein said support piece has a plurality of radially extending members that contact internal wall surfaces of said housing such that said support piece makes discontinuous contact with said internal wall surfaces around a periphery of said support piece.

8. The apparatus of claim 7, further comprising a removable end cap adapted to surround the needle and close said opening while retaining the needle within said chamber.

9. An apparatus for dispensing a material during a dental or endodontic procedure, comprising:
   a housing including a motor with an output, said housing further including a proximal end and a distal end extending along a longitudinal axis,
   a switch coupled with said housing and configured to operate said motor,
   a needle heating member including a chamber extending around the longitudinal axis proximate the distal end,
   an opening in said housing at the distal end extending around the longitudinal axis, said opening communicating with said chamber and configured to receive a disposable needle prefilled with the material,
   a plunger coupled with said motor and configured to expel the material from the needle during activation of said motor,
   a heating element thermally coupled with said needle heating member and at least substantially surrounding said chamber for heating the material in the needle, and
   a removable, autoclavable sheath surrounding at least a portion of said housing, said sheath comprising a first, rigid member and a second, resilient member at least partially overlying said first, rigid member and adapted to be gripped by a user while dispensing the material, said first, rigid member including a window overlying said switch and said second, resilient member including a switch area overlying said window and capable of being depressed for operating said switch.

* * * * *